United States Patent
Meloy et al.

(10) Patent No.: US 6,169,924 B1
(45) Date of Patent: Jan. 2, 2001

(54) SPINAL CORD STIMULATION

(75) Inventors: T. Stuart Meloy, 2918 Hwy. 601 South, Mocksville, NC (US) 27028; W. Joseph Martin, Mocksville, NC (US)

(73) Assignee: T. Stuart Meloy, Mocksville, NC (US)

( * ) Notice: Under 35 U.S.C. 154(b), the term of this patent shall be extended for 0 days.

(21) Appl. No.: 09/300,584

(22) Filed: Apr. 27, 1999

(51) Int. Cl.[7] ..................................................... A61N 1/02
(52) U.S. Cl. ............................................................ 607/39
(58) Field of Search ............................... 607/1, 2, 39–41

(56) References Cited

U.S. PATENT DOCUMENTS

| | | |
|---|---|---|
| 742,814 | 10/1903 | Todd . |
| 2,932,297 | 4/1960 | Provenza . |
| 3,941,136 | 3/1976 | Bucalo . |
| 4,515,167 | * 5/1985 | Hochman ................................ 607/39 |
| 4,585,005 | 4/1986 | Lue et al. . |
| 4,633,889 | 1/1987 | Talalla et al. . |
| 5,417,719 | 5/1995 | Hull et al. . |
| 5,454,840 | 10/1995 | Krakorsky et al. . |
| 5,643,330 | 7/1997 | Holsheimer et al. . |

OTHER PUBLICATIONS

Spinal Cord Stimulation Percutaneous Lead Implantation Guide; Medtronic, Inc. 1997.

* cited by examiner

Primary Examiner—George R. Evanisko
(74) Attorney, Agent, or Firm—Rhodes & Mason, P.L.L.C.

(57) ABSTRACT

The present invention provides a method for spinal cord stimulation to treat orgasmic dysfunction. Stimulating electrodes are placed in the spinal canal via a needle inserted between the appropriate vertebrae in parallel with the spinal cord. The electrodes are connected to a power source. Through variable transmission of electrical signals a patient suffering from orgasmic dysfunction may once again achieve orgasm.

15 Claims, 3 Drawing Sheets

SPINAL CORD STIMULATION

FIELD OF THE INVENTION

The present invention generally relates to therapy by spinal cord stimulation and more particularly relates to spinal cord stimulation for the treatment of orgasmic dysfunction.

BACKGROUND

Orgasmic dysfunction is an inhibition of the orgasmic phase of the sexual response cycle. Orgasmic dysfunction is a serious disorder that plagues both women and men. Like all dysfunctions, orgasmic dysfunction may be life long or acquired. The condition is referred to as primary (life-long) when the patient has never experienced orgasm through any means of stimulation. The problem is considered secondary (acquired) if the patient has attained orgasm is the past but is currently non-orgasmic. Situational orgasmic dysfunction in women refers to a woman who can climax through some methods of stimulation, but not through others. The American Psychiatric Association describes the disorder as the "persistent or recurrent delay in, or absence of, orgasm following a normal sexual excitement phase during sexual activity."

The general theory of normal sexual response cycle involves three phases: desire, excitement, and orgasm. Metaphorically, each phase of the normal sexual response may be thought to have a common generator but each phase also has its own circuitry. This separate neural circuitry creates the possibility for separate and discrete inhibition of the three phases. Certain kinds of trauma, if sufficiently intense, disturb the entire system, but often only one component is disrupted.

Orgasmic dysfunction should be distinguished from the excitement phase of the sexual response cycle. The excitement phase involves the arousal or erection of the sexual organs. There currently are several products, both drug-induced and mechanical, to stimulate and induce the excitement phase.

For example, to treat impotence (also called erectile dysfunction) it is known to implant electrical conductors to the surface of the pelvic splanchnic nerve. Stimulation of this nerve with low voltage electrical pulses is believed to causes arterioles dilation and initiate erection. Also, it is known that implantation of an electrode on the cavernous nerves of a male, adjacent to his prostate gland, may also achieve penile erection. Further, other electrical impulse devices exist that are not implanted but instead applied topically to the coccyx region to promote sexual excitation. Impotence, however, should not be confused with orgasmic dysfunction where satisfactory erection may be obtained but there is an absence of orgasm.

Current treatment of orgasmic dysfunction concentrates on the psychological components of the disorder rather than the physiological components. Orgasmic dysfunction is a physical malady that results in marked distress and interpersonal difficulty. The physical disorder causes psychological performance anxiety and pressure. Sexual desire and frequency usually decline. The patient's intimate relationships ultimately suffer from resentment and conflict.

Although psychological therapy may be required to rebuild confidence and regain the phases of desire and excitement, the orgasm phase requires a physiological solution. A basic tenet of most sex therapies is that an actual physical response will alleviate much of the anxiety associated with the disorder and initiate a positive mental response regarding the other two stages of the sexual cycle. Although it is important in treatment to improve communication and enhance relationships, an initial objective in therapy is the ability to obtain orgasm under any circumstances.

Within the neuromodulating community, there is anecdotal evidence of patients who have experienced mild sensation of the genitalia while undergoing spinal cord stimulation for pain relief.

Spinal cord stimulation, on the other hand, has been used as a treatment for chronic painful conditions for approximately thirty years. Commonly, spinal cord stimulation is used to alleviate pain after failed surgery, pain due to neuropathies, or pain due to inadequate blood flow. Neurostimulation systems have been found to relieve chronic, intractable pain in the limbs or trunk.

The basic concept of neurostimulation as it relates to pain relief involves the substitution of sensations that reach the thalamus of the brain. Rather than a pain message, the spinal cord stimulation closes the gate in the spinal cord and replaces the pain sensation with a tingling sensation. Electrodes are positioned effectively to create parathesia in the painful area.

Parathesia refers to a change in sensation in an area of the body. Usually parathesia is used to show change in neurologic function caused by damage to a nerve or nerves. Parathesia is usually not an absence of sensation but a decrease or alteration of sensation. Patients have described parathesia as a "buzzing sensation."

Parathesia is accomplished through the implantation of stimulating electrodes within the spinal canal. The electrodes are inserted between the vertebrae in parallel with the spinal cord. Low-voltage electrical stimulation is precisely applied to the spinal cord. Through direct stimulation of the dorsal column or the targeted peripheral nerve, the sensation of pain is replaced by a more pleasant "tingling" sensation.

The sensation can be adjusted in terms of amplitude to control intensity, pulse width to control duration and frequency. Further, the neurostimulation system is implantable in its entirety. Medtronic Neurological, a division of Medtronic, Inc. of Minneapolis, Minn. sells a neurostimulator system used for pain relief. The device has been approved by the Federal Drug Administration for implantation in the spinal cord to effectively alleviate pain.

Heretofore, spinal cord stimulation has not been used to treat orgasmic dysfunction. There exists a need, however, to effectively treat orgasmic dysfunction through a physiological approach.

SUMMARY

The present invention for the first time, recognizes that carefully placed and controlled spinal cord stimulation may be used to treat orgasmic dysfunction. Stimulating electrodes are placed in the spinal canal via a needle inserted between the appropriate vertebrae in parallel with the spinal cord. The electrodes are connected to a power source. Through variable transmission of radio frequency waves a patient suffering from orgasmic dysfunction may once again achieve orgasm.

The stimulator may be entirely implanted within the patient's body. The device is controllable in a variety of ways. Current stimulators for pain have the ability to vary according to a 24-hour clock. The device may be equipped with a controller operable by the patient. It is possible to program the device to deliver an arbitrarily limited number of stimulations of predetermined length to prevent overstimulation.

DETAILED DESCRIPTION OF THE PREFERRED EMBODIMENT

The implantation of spinal cord systems is generally known and has a standard clinical procedure to effectuate pain relief. For example, the Medtronic Itrel and X-trel neurostimulation system for spinal cord stimulation is indicated for the management of chronic pain of the trunk or limbs. Also from Medtronic, the X-Tel and Matrix Receiver Model 3272 systems are also indicated for peripheral nerve stimulation and pain relief. With regard to the present invention however, the procedure differs in the indications for the implantation procedure and the electrode level on the vertebrae. The following represents a description sufficient to allow one skilled in the art to practice the invention. If needed for reference, the standard implantation procedure of neurostimulation systems is described in greater detail in the *Spinal Cord Stimulation: Percutaneous Lead Implantation Guide*, Medtronic, Inc. 1997, a clinical guide published by Medtronic Neurological, the disclosure of which is here incorporated by reference.

Figure 1:
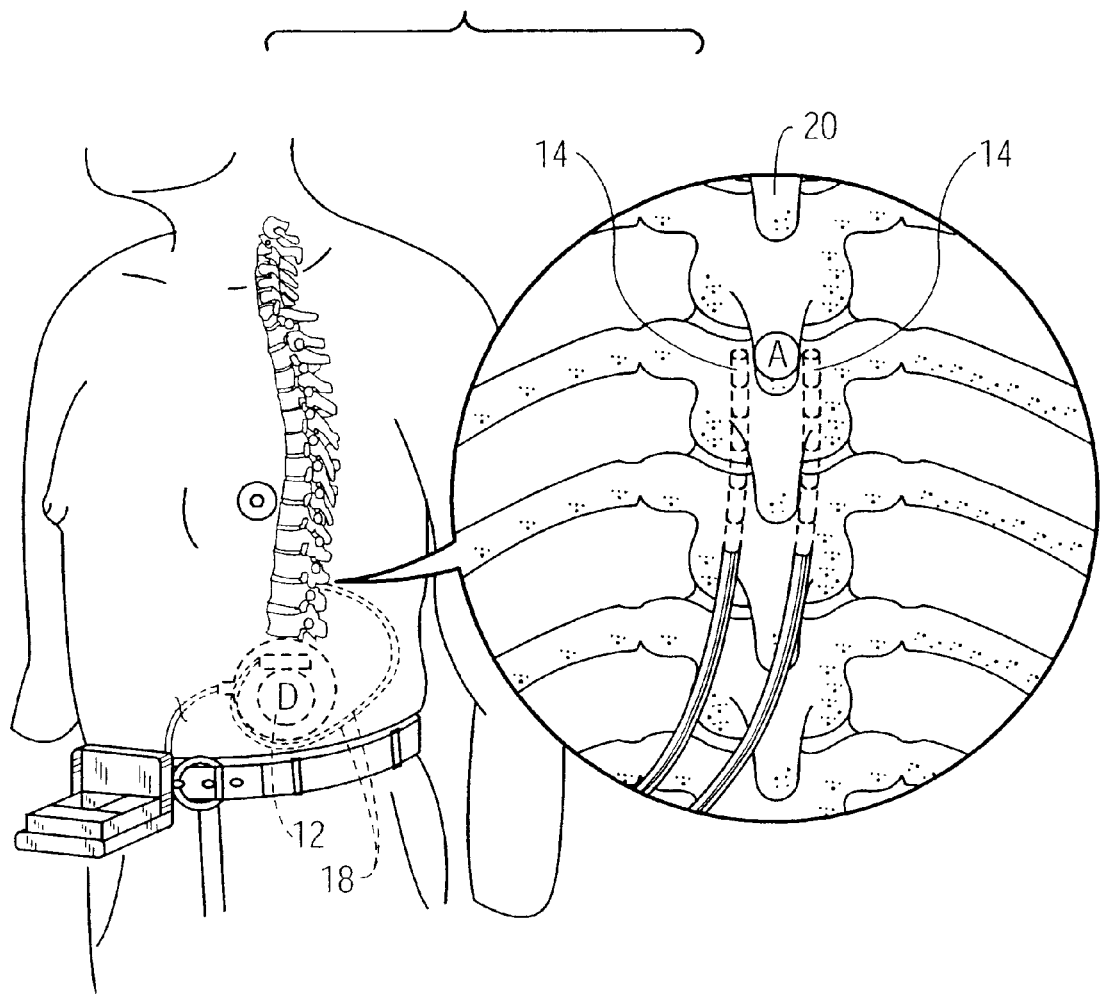
FIG. 1 is a perspective view of the spinal cord stimulator implanted in a patient with a cut out sectional of the spinal cord.

FIG. 1 illustrates the spinal cord stimulator as implanted in a patient with a cross sectional view of a spinal cord as is known in the art. The preferred system employs an implantable pulse generator 12 with insulated extensions to produce independent stimulation pulses which are sent to the spinal cord 20 through at least one insulated lead 14 that is coupled to the spinal cord 20 through electrodes located at point A. After implantation, an external controller 15 transmits signals through the patient's skin to the pulse generator 12. The pulse generator 12 receives either radio frequency or magnetic influence from the external controller 15 and sends electrical impulses to the spinal cord 20 to control the patient's orgasm.

Figure 2:
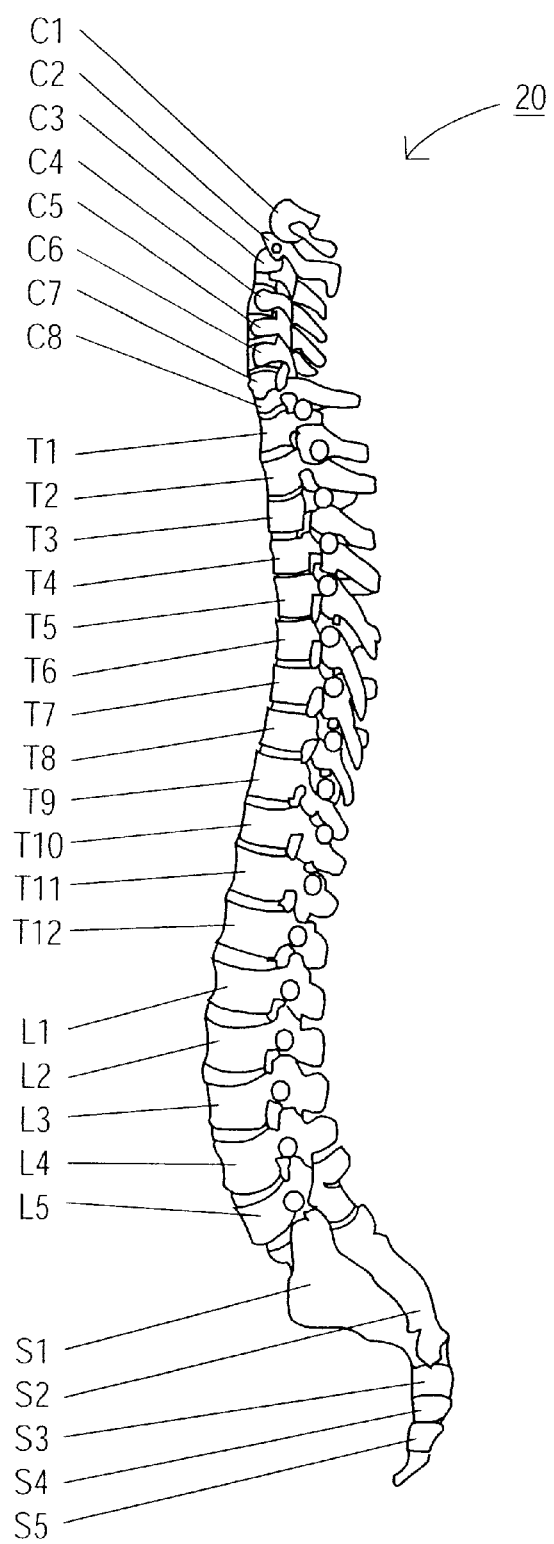
FIG. 2 is a cross sectional view of a spinal cord.

As seen in FIG. 2, the spinal cord is divided into specific neurological segments. The cervical spinal cord is divided into eight levels and contributes to different functions in the neck and arms. In the thoracic region the nerves of the spinal cord supply muscles of the chest. This region also contains nerves in the sympathetic nervous system. The lumbosacral spinal cord and nerves supply legs, pelvis and bowel and bladder.

The range of electrode placement may range between about the eighth thoracic level (T-8) and the third sacral level (S-3), inclusive of the lumbar vertebra levels. The entry level for this preferred range would therefore be at about the third lumbar level (L-3). If necessary, a caudal approach may be taken.

A more preferred range of electrode placement lies between about the eleventh thoracic level (T-11) and the second lumbar level (L-2). An entry level of the third lumbar level (L-3) would be preferable for this range. The exact position of the electrodes, however, is variable and unique among patients and is determined more precisely at the time of implantation.

The present invention is indicated by orgasmic dysfunction in either men or women.

Figure 3A:
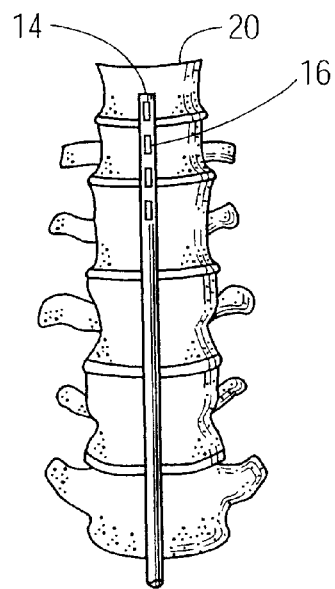
FIGS. 3a and 3b are fluoroscopic views of single and dual leads, respectively, in a patient's epidural space.
Figure 3B:
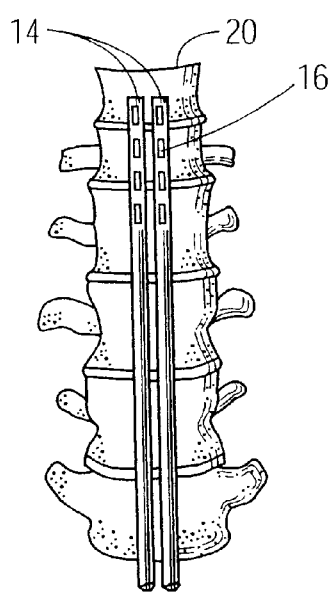

A stimulating, insulated lead 14 is implanted into a patient's epidural space. As seen in FIGS. 3a and 3b, either single or dual leads may be placed within the epidural space as warranted by the individual patient's needs. At the tip of the lead 14 there are four electrodes 16 to carry electrical impulses. As outlined above, an entry level of approximately L-3 and a lead tip level in the range from about T-8 through S-3 are preferred. A lead level of T-11 through L-2 upon entry from L-3 is most preferred.

Upon placement, electrical stimulation should be supplied in an effective amount to achieve genital stimulation and orgasm. As used herein "effective amount" is variable among patients but generally corresponds within a rate range of approximately 2.1 to 130 pulses per second, a pulse width range of approximately 60 to 450 milliseconds, and an amplitude range of approximately up to 10 volts.

The testing lead position is tested to match a stimulation pattern and effective amount to the patient's orgasmic nerve distribution. As stated, the exact effective position of the electrodes is variable and unique among patients. The lead 14 is secured for trial screening of the patient's response to stimulation. A percutaneous extension is connected to the implanted and secured to the lead 14 and external percutaneous wires are connected. A patient then goes through a trial-screening period where the patient is evaluated in an awake and active state for stimulation effectiveness. Should the trial screening period prove ineffective the leads may be repositioned. Should the patient not wish to proceed, the leads and percutaneous extension may be removed. Should the trial screening period be positive (at least 50% effective and patient demonstrates desire to proceed), the spinal cord stimulation system is internalized within the patient.

For internalization, the percutaneous extension is removed. A neurostimulator 12 and an extension 18 for connection of the neurostimulator and the lead are then implanted. Preferably the neurostimulator 12 is implanted in the patient's abdomen. Thereafter, the spinal cord stimulation system is operative to induce orgasm upon activation of the neurostimulator.

The following represent examples of genital stimulation through spinal cord stimulation. It must be emphasized, however, that the exact effective position of the electrodes is variable and unique among patients and is determined more precisely at the time of implantation. For instance, Example 2 occurred when the electrode was initially inserted at an effective level for pain relief but became displaced over time to a point that induced genital stimulation.

| Lead Placement | #1 Lead | #2 Lead | Rate | Pulse Width | Amplitude |
| --- | --- | --- | --- | --- | --- |
| T-11 | Positive | Negative | 100 pps | 250 ms | 0.4 V |

The patient vocalized intense genital stimulation without discomfort.

EXAMPLE 2

Displacement

A patient had a spinal cord stimulator implanted for relief of left hip pain. The lead had become displaced and relocated at the T-11 level. The patient experienced genital stimulation rather than pain relief.

EXAMPLE 3

Prophetic

As stated, the necessary specifications of lead placement, rate, pulse width, and amplitude are variable among patients. Each patient must be tested for individual response among the above-stated variables.

For example, a patient may respond positively to lead placement at the T-8 level. The rate is set for 130 pulses per second, the pulse width is set at 60 milliseconds and the amplitude is set to 0.1 volts. Additionally, the patient may respond positively to S-3 placement with a rate of 2.1 pulses per second, a pulse width of 60 milliseconds, and amplitude of 10 volts.

Once the lead is placed, the patient should be subjected to a range of variables to determine the most appropriate. Each patient should also undergo a trial screening period to determine sustained effectiveness once the variables are set.

As a hypothetical example consider a 65-year-old female who suffers from obesity and is further troubled by traumatic avulsion of both the anterior and posterior cruciate ligaments of the left knee. Because of her body habitus and knee injury, she is unable to engage in sexual relations with her husband nor increase her metabolic rate to lose weight. She does desire to experience sexual climax. An initial stimulation site at the L2–3 level with lead 1 positive and lead 2 negative, a pulsewidth of 200 and a rate of 100 PPS may be inserted. The initial voltage level would be zero but would be increased incrementally in 0.10 V steps. Again, due to individual variables, sustained effectiveness should be appropriately tested and adjusted as necessary.

While the invention has been particularly shown and described with reference to a preferred embodiment thereof, it will be understood by those skilled in the art that various changes in form and details may be made therein without departing from the spirit and scope of the invention.

We claim:

1. A method for treating orgasmic dysfunction comprising:
   supplying electrical stimulation to a selected area of the spinal cord of a patient in an effective amount to achieve genital stimulation and orgasm.

2. The method of claim 1 wherein the genital stimulation induces orgasm.

3. The method of claim 1 wherein the selected area is T-8–S-3, inclusive of the lumbar.

4. The method of claim 1 wherein the selected area is T-1–L-2.

5. The method of claim 1 further comprising:
   implanting the tip of at least one insulated lead at said selected area of the patient's spinal cord at a spot that effectively corresponds to the patient's genitalia;
   transmitting electrical impulses to the at least one lead whereby each of the at least one lead carries electrical impulses to stimulate spinal nerves to induce orgasm.

6. The method of claim 5 wherein the selected area is T-11, two insulated leads are implanted with opposite electrical charges and the electrical impulses are transmitted at 100 Hz and 0.4 V through 250 milliseconds.

7. The method of claim 1 further comprising:
   implanting at least one insulated lead at said selected area of the patient's spinal cord at a spot that corresponds to the patient's genitalia;
   implanting an implantable pulse generator
   transmitting signals from an external controller through the patient's skin to said implantable pulse generator in the patient whereby the pulse generator receives the signals and in turn sends electrical impulses to the spinal cord to cause the patient's orgasm.

8. The method of claim 1 further comprising:
   implanting an implantable pulse generator that supplies energy for stimulation in the patient;
   connecting an insulated extension to the implantable pulse generator;
   implanting at least one lead at said selected area of the spinal cord at a spot that corresponds to the patient's genitalia and thereafter connecting the at least one lead to the insulated extension;
   stimulating spinal nerves with electrical impulses supplied by the implantable pulse generator whereby orgasm is achieved.

9. A method for treating orgasmic dysfunction comprising:
   implanting at least one stimulating lead into a patient's epidural space wherein the at least one lead has a tip with four electrodes to carry electrical impulses with an entry level of approximately lumbar level three and a lead tip level in the range from about thoracic level ten through sacral level three;
   testing the at least one lead position to match a stimulation pattern to the patient's orgasmic nerve distribution;
   securing the at least one lead for trial screening of the patient's response to stimulation;
   connecting a percutaneous extension to the implanted and secured at least one lead;
   externalizing percutaneous wires for trial screening of the patient's response to stimulation;
   screening the patient for a trial period wherein the patient is evaluated in an awake and active state for stimulation effectiveness; and
   internalizing a spinal cord stimulation system if the trial screening period is positive by removing the percutaneous extension, implanting a neurostimulator and an extension for connection with the at least one lead whereby the spinal cord stimulation system is operative to induce orgasm upon activation of the neurostimulator.

10. The method of claim 9 further including:
    repositioning the at least one lead after testing.

11. The method of claim 9 further including:
    removing the at least one lead and percutaneous extension if the trial screening is negative.

12. The method of claim 9 further including: the neurostimulator activating by a magnet.

13. The method of claim 9 further including: the neurostimulator is activating by a patient programmer.

14. A method for treatment of orgasmic dysfunction comprising:
    effectively stimulating a patient's spinal cord at a spot that corresponds to the patient's genitalia to induce orgasm.

15. The method of claim 14 further comprising:
    supplying the effective stimulation with an electrical impulse whereby orgasm is achieved through electrical stimulation.

* * * * *

UNITED STATES PATENT AND TRADEMARK OFFICE
CERTIFICATE OF CORRECTION

PATENT NO. : 6,169,924 B1
DATED : January 2, 2001
INVENTOR(S) : T. Stuart Meloy and W. Joseph Martin Page 1 of 1

It is certified that error appears in the above-identified patent and that said Letters Patent is hereby corrected as shown below:

<u>Column 5, claim 4,</u>
Change "T-1-L2" to -- T-11-L2 --.

Signed and Sealed this

Twenty-fifth Day of September, 2001

Attest:

NICHOLAS P. GODICI
*Attesting Officer*    *Acting Director of the United States Patent and Trademark Office*